(12) United States Patent
Johnson

(10) Patent No.: US 9,816,142 B2
(45) Date of Patent: Nov. 14, 2017

(54) **COMPOSITIONS AND METHODS FOR DETECTION OF *STAPHYLOCOCCUS AUREUS***

(71) Applicant: Roche Molecular Systems, Inc., Pleasanton, CA (US)

(72) Inventor: Jenny A. Johnson, Castro Valley, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 72 days.

(21) Appl. No.: 14/687,813

(22) Filed: Apr. 15, 2015

(65) Prior Publication Data

US 2015/0218622 A1 Aug. 6, 2015

Related U.S. Application Data

(63) Continuation of application No. 13/116,975, filed on May 26, 2011, now Pat. No. 9,034,581.

(51) Int. Cl.
*C12P 19/34* (2006.01)
*C12Q 1/68* (2006.01)

(52) U.S. Cl.
CPC ........ *C12Q 1/689* (2013.01); *C12Q 2600/112* (2013.01); *C12Q 2600/118* (2013.01)

(58) Field of Classification Search
CPC ............... C12C 1/689; C12C 2600/112; C12C 2600/118
USPC ........................................................ 435/91.2
See application file for complete search history.

(56) References Cited

U.S. PATENT DOCUMENTS

| | | | |
|---|---|---|---|
| 2006/0115490 A1* | 6/2006 | Masignani | C07K 14/31 424/190.1 |
| 2007/0031850 A1 | 2/2007 | Mounts et al. | |
| 2010/0055130 A1 | 3/2010 | Masignani et al. | |

FOREIGN PATENT DOCUMENTS

| | | |
|---|---|---|
| EP | 0866071 B1 | 10/2004 |
| WO | 2005014857 A2 | 2/2005 |
| WO | 2005014857 A3 | 2/2005 |
| WO | 2005108579 A1 | 11/2005 |
| WO | PCT/EP2012/002242 | 9/2012 |

OTHER PUBLICATIONS

XP002681533, 2007, "Human polymorphism genotyping probe SEQ ID No. 104497", Database accession No. AEU33850 relevant for SEQ ID No. 2.
XP002681534, 2011, "Weal eDNA 3690", Database accession No. ARJ90380 the whole document relevant for SEQ ID No. 3.
XP002681540, 2010, "*S. aureus* NCTC 8325 derived immunogenic protein encoding DNA SEQ ID No. 2665", Database accession No. AXV81841.
XP002681541, 2009, "Sequence 219 from Patent W02005014857", Database accession No. HA 149352.
Killgore et al., "A 5' Nuclease PCR (TaqMan) High-Throughput Assay for Detection of the mecA Gene in Staphylococci," Journal of Clinical Microbiology, Jul. 2000, vol. 38, No. 7, pp. 2516-2519.
Marras et al., "Real-time assays with molecular beacons and other fluorescent nucleic acid hybridization probes," Clinia Chimica Acta, 2006, vol. 363, pp. 48-60.
Heid et al., "Real Time Quantitative PCR," Genome Research, 1996, vol. 6, pp. 986-994.
Elsayed et al., "Development and Validation of a Molecular Beacon Probe-Based Real-Time Polymerase Chain Reaction Assay for Rapid Detection of Methicilin Resistance in *Staphylococcus aureus*," Arch. Pathol. Lab Med, 2003, vol. 127, pp. 845-849.
Deurenberg et al., "Rapid detection of Panton-Valentine leukocidin from clinical isolates of *Staphylococcus aureus* strains by real-time PCR," FEMS Microbiology, 2004, vol. 240, pp. 225-228.

\* cited by examiner

*Primary Examiner* — Cynthia B Wilder
(74) *Attorney, Agent, or Firm* — David J. Chang; M. Reza Savari

(57) ABSTRACT

The present invention relates to methods for the rapid detection of the presence or absence of *Staphylococcus aureus* in a biological or nonbiological sample. The present invention includes methods of detection comprising performing an amplifying step, a hybridizing step, and a detecting step. Furthermore, the present invention relates to primers, probes, and kits that are designed for the detection of *Staphylococcus aureus*.

5 Claims, 4 Drawing Sheets atgagaaaaa atattttaat tacaggcgta catggatata tcggtaatgc tttaaaagat    60
aagcttattg aacaaggaca tcaagtagat caaattaatg ttaggaatca attatggaag    120
tcgacctcgt tcaaagatta tgatgtttta attcatacag cagctttggt tcacaacaat    180
tcacctcaag caaggctatc tgattatatg caagtgaata tgttgctgac gaaacaattg    240
gcacaaaagg ctaaagctga agacgttaaa caatttattt ttatgagtac tatggcagtt    300
tatggaaaag aaggtcatgt tggtaaatca gatcaagttg atacacaaac accaatgaac    360
cctacgacca actatggtat ttccaaaaag ttcgctgaac aagcattaca agaattgatt    420
agtgattcgt ttaaagtagc aattgtgaga ccaccaatga tttatggtgc acattgccca    480
ggaaatttcc aacggttaat gcaattgtca aagcgattgc caatcattcc caatattaac    540
aatcagcgca gtgcattata tattaaacat ctgacagcat ttattgatca attaatatca    600
ttagaagtga caggtgtgta ccatcctcaa gatagttttt actttgatac atcgtcagta    660
atgtatgaaa tacgtcgcca atcacatcgt aaaacggtat tgatcaacat gccttcaatg    720
ctaaataagt attttaataa gttgtcggtc tttagaaaat tattcggcaa tttaatatac    780
agcaatacgt tatatgaaaa taataatgca cttgaaatta ttcctggaaa aatgtcactt    840
gttattgcgg acatcatgga tgaaacgaca accaaagata aggcataa           888

(SEQ ID NO: 1)

FIGURE 1

ACACCAATGAACCCTACGACCAACTATGGTATTTCCAAAAAGTTCGCTGAACA
AGCATTACAAGAATTGATTAGTGATTCGTTTAAAGTAGCAATTGTGAGACCAC
CAATGATTTATGGTGCACATTGCCCAGGAAATTTCCAACGGTTAATGCAATTG
TCAAAGCGATTGCCAATCATTCCCAATATTAACAATCAGCGCAGTGCATTATA
TATTAAACATCTGACAGCATTTATTGATCAATTA (SEQ ID NO: 5)

FIGURE 2A

ACACCAATGAACCCTACGACCAACTATGGTATTTCCAAAAAGTTCGCTGAACA
AGCATTACAAGAATTGATTAGTGATTCGTTTAAAGTAGCAATTGTGAGACCAC
CAATGATTTATGGTGCACATTGCCCAGGAAATTTCCAACGGTTAATGCAATTG
TCAAAGCGATTGCCAATCATTCCCAATATTAACAATCAGCGCAGTGCATTATA
TATTAAACATCTGACAGCATTTATTGATCAATTA (SEQ ID NO: 7)

FIGURE 2B

GATAAGCTTATTGAACAAGGACATCAAGTAGATCAAATTAATGTTAGGAATCA
ATTATGGAAGTCGACCTCGTTCAAAGATTATGATGTTTTAATTCATACAGCAGC
TTTGGTTCACAACAATTCACCTCAAG (SEQ ID NO: 11)

FIGURE 2C

AAGATAAGCTTATTGAACAAGGACATCAAGTAGATCAAATTAATGTTAGGAAT
CAATTATGGAAGTCGACCTCGTTCAAAGATTATGATGTTTTAATTCATACAGCA
GCTTTGGTTCACAACAATTCACCTCAAG (SEQ ID NO: 13)

FIGURE 2D

COMPOSITIONS AND METHODS FOR DETECTION OF *STAPHYLOCOCCUS AUREUS*

CROSS-REFERENCES TO RELATED APPLICATIONS

This application is a continuation of application Ser. No. 13/116,975, filed on May 26, 2011, now U.S. Pat. No. 9,034,581, the entire content of which is hereby incorporated herein by reference in its entirety.

FIELD OF THE INVENTION

The present invention relates to the field of microbial diagnostic, and more particularly, to detection of *Staphylococcus aureus*.

BACKGROUND OF THE INVENTION

*Staphylococcus aureus* ("*S. aureus*" or "SA") is a facultative anaerobic, Gram-positive bacterium, whose natural reservoir includes the human skin and nose and can also inhabit wounds. Most people who carry *S. aureus* show no sign of infection; however, *S. aureus* can become invasive and cause infection in the body if the normal barrier is breached. *S. aureus* can cause a number of illnesses ranging from minor skin infections such as pimples, boils, and abscesses, to major diseases such as pneumonia, meningitis, and sepsis. Tissues other than skin and nose can be infected when barriers are breached, e.g., skin or mucosal lining, which leads to furuncles and carbuncles. *S. aureus* infections can spread between people through skin contact with an infected person or contact with objects used by an infected person.

*S. aureus* posses a remarkable ability to develop resistance to the major antibiotics, including the penicillins (methicillin, oxacillin, cloxacillin and flucloxacillin), which has earned it the label "superbug". Methicillin-resistant *S. aureus* (MRSA) is a bacterium that has become resistant to penicillins, and it is responsible for several human infections that are difficult to treat. MRSA may also be known as oxacillin-resistant *S. aureus* (ORSA) and multiple-resistant *S. aureus*, while the non-methicillin resistant strains of *S. aureus* are sometimes called methicillin-sensitive *S. aureus* (MSSA).

Diagnosis of *S. aureus* infection can include a physician evaluation of a patient's symptoms, which is normally not definitive because the infection may have been caused by another bacterium, such as *Streptococcus pyogenes*. Blood tests, urine analysis, and sometimes x-rays can be used to diagnose *S. aureus* infections. A definitive diagnosis may require a culture test, which can only be obtained after many hours or days, delaying the patient's treatment.

Certain PCR assays have been developed that are designed for the specific detection of MRSA due to its increased clinical significance in hospital and community acquired diseases. Literature indicates, however, that there is also significant clinical need to detect *S. aureus* whether or not it is antibiotic resistant.

SUMMARY OF THE INVENTION

The present invention relates to methods for the rapid detection of the presence or absence of *S. aureus* in a biological or nonbiological sample. The present invention includes methods of detection comprising performing at least one cycling step, which includes an amplifying step and a hybridizing step. Furthermore, the present invention relates to primers, probes, and kits that are designed for the detection of *S. aureus*. The gene targeted in the methods of the present invention for the detection of *S. aureus* is a Capsular Polysaccharide Enzyme (CPE) gene. For example, the CPE gene target cap5N was chosen because it was determined to be specific to *S. aureus* and not present in other *Staphylococcal* species, and also and demonstrated good homology within *S. aureus*. The CPE gene has an unconfirmed function as a reductase enzyme in the pathway to produce *S. aureus* capsular polysaccharide (O'Riordan et al., 2004, *Clin. Microbiol. Rev.* 17(1):218-234).

In one aspect, the present invention provides an oligonucleotide comprising or consisting of a sequence of nucleotides selected from SEQ ID NOs: 2-4, 6, 8-10, 12, and 14-34 or a complement thereof, which oligonucleotide has 100 or fewer nucleotides. In another aspect, the present invention provides an oligonucleotide that includes a nucleic acid having at least 70% sequence identity (e.g., at least 75%, 80%, 85%, 90% or 95%, etc.) to one of SEQ ID NOs: 2-4, 6, 8-10, 12, and 14-34, or a complement thereof, which oligonucleotide has 100 or fewer nucleotides. Generally, these oligonucleotides may be primer nucleic acids, probe nucleic adds, or the like in these embodiments. In certain of these embodiments, the oligonucleotides have 40 or fewer nucleotides (e.g., 35 or fewer nucleotides, 30 or fewer nucleotides, etc). In some embodiments, the oligonucleotides comprise at least one modified nucleotide, e.g., to alter nucleic add hybridization stability relative to unmodified nucleotides. Optionally, the oligonucleotides comprise at least one label and/or at least one quencher moiety. In some embodiments, the oligonucleotides include at least one conservatively modified variation.

In a further aspect, the present invention provides a method for detecting SA in a sample, the method comprising performing an amplifying step comprising contacting the sample with a set of SA CPE primers to produce an amplification product if SA is present in the sample; performing a hybridizing step comprising contacting the amplification product with one or more detectable SA CPE probes; and detecting the presence or absence of the amplified product, wherein the presence of the amplified product is indicative of the presence of SA in the sample and wherein the absence of the amplified product is indicative of the absence of SA in the sample. In one embodiment, each primer of the set of SA CPE primers comprises or consists of a sequence of nucleotides, selected from the group consisting of SEQ NOs: 2, 3, 6, 8, 9, 12, and 14-26, or a complement thereof; and wherein the one or more detectable SA CPE probes comprise or consists of a sequence of nucleotides selected from the group consisting SEQ ID NOs: 4, 10, and 27-34, or a complement thereof. In some embodiments, a hybridizing step includes contacting the amplification product with a probe that is labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the probe. The presence or absence of fluorescence is indicative of the presence or absence of SA in the sample.

In one aspect, amplification can employ a polymerase enzyme having 5' to 3' exonuclease activity. Thus, the first and second fluorescent moieties may be within no more than 5 nucleotides of each other along the length of the probe. In another aspect, the SA probe includes as nucleic acid sequence that permits secondary structure formation. Such secondary structure formation generally results in spatial proximity between the first and second fluorescent moiety. According to this method, the second fluorescent moiety on the probe can be a quencher.

In a further aspect, the present invention provides a kit for detecting a nucleic acid of SA. The kit can include a first oligonucleotide comprising or consisting of a sequence selected from the group consisting of SEQ ID NOs: 2, 8, 12, and 14-20, or a complement thereof; a second oligonucleotide comprising or consisting of a sequence selected from the group consisting of SEQ ID NOs: 3, 6, 9, and 2-26, or a complement thereof; and a third detectably labeled oligonucleotide comprising or consisting of a sequence selected from the group consisting of SEQ ID NOs: 4, 10, and 27-34, or a complement thereof.

In one aspect, the kit can include probes already labeled with donor and corresponding acceptor fluorescent moieties, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of SA in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 1 shows the reference gene sequence of the cap5N *Staphylococcus aureus* Capsular Polysaccharide Enzyme gene.

FIG. 2A-2D show amplicon sequences for *Staphylococcus aureus*, each including the upstream primer (▬), downstream primer (▭), and probe (⋯).

DETAILED DESCRIPTION OF THE INVENTION

Figure 3A:
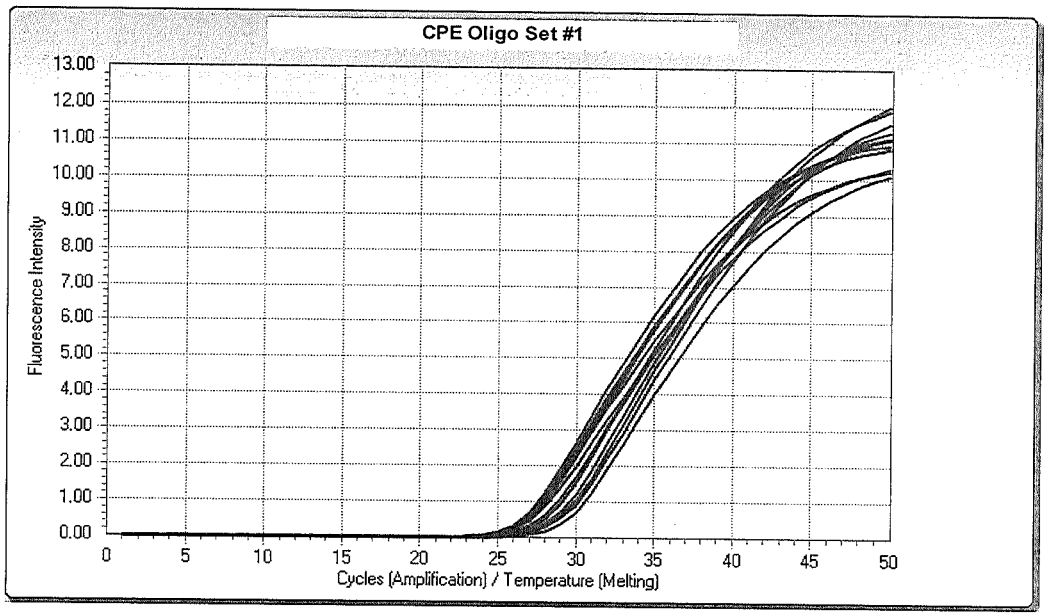
FIG. 3A-3D show amplification curves for detection of *Staphylococcus aureus*.

A real-time assay for detecting *S. aureus* in a sample is described herein. The present invention provides for methods of detecting *S. aureus*, whether or not it is methicillin resistant. Primers and probes for detecting *S. aureus* are provided, as are articles of manufacture or kits containing such primers and probes. The increased sensitivity of real-time PCR for detection of *S. aureus* compared to other methods, as well as the improved features of real-time PCR including sample containment and real-time detection of the amplified product, make feasible the implementation of this technology for routine diagnosis of *S. aureus* infections in the clinical laboratory.

The methods include performing at least one cycling step that includes amplifying a portion of a SA CPE nucleic acid molecule from a sample using a pair of CPE primers. "CPE primers" as used herein refers to oligonucleotide primers that specifically anneal to nucleic acid sequences encoding CPE, and initiate synthesis therefrom under appropriate conditions. Each of the CPE primers anneals to a target within or adjacent to a CPE nucleic acid molecule such that at least a portion of each amplification product contains nucleic acid sequence corresponding to CPE. The CPE amplification product is produced provided that CPE nucleic acid is present in the sample, thus the presence of the CPE amplification product is indicative of the presence of SA in the sample. The amplification product should contain the nucleic acid sequences that are complementary to one or more detectable CPE probes. Each cycling step includes an amplification step, as hybridization step, and a detection step, in which the sample is contacted with the one or more detectable CPE probes for detection of the presence or absence of SA in the sample.

As used herein, the term "amplifying" refers to the process of synthesizing nucleic acid molecules that are complementary to one or both strands of a template nucleic acid molecule (e.g., SA CPE nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g. $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe" according to the invention.

The term "hybridizing" refers to the annealing of one or more probes to an amplification product. Hybridization conditions typically include a temperature that is below the melting temperature of the probes but that avoids non-specific hybridization of the probes.

The term "5' to 3' exonuclease activity" refers to an activity of a nucleic add polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures or the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic add sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:66-272, Madden et al. (1996) "Applications of network BLAST server" *Meth. Enzymol,* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the invention are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments of the invention. Examples of these types of nucleic acid modifications are described in, e.g., U.S. Pat. No. 6,001,611, which is incorporated herein by reference.

*S. aureus* Nucleic Acids and Oligonucleotides

The invention provides methods to detect SA by amplifying, for example, a portion of the SA CPE gene nucleic acid. Nucleic acid sequences from SA are available (see, for example, GenBank Accession No. NC_002745). Specifically, primers and probes to amplify and detect SA CPE nucleic acid molecules are provided by the present invention.

For detection of SA, primers and probes to amplify CPE nucleic acid molecules are provided. CPE nucleic acids other than those exemplified herein can also be used to detect SA in a sample. For example, fictional variants can be evaluated for specificity and/or sensitivity by those of skill in the art using routine methods. Representative functional variants can include, e.g., one or more deletions, insertions, and/or substitutions in the CPE nucleic acids disclosed herein.

More specifically, the oligonucleotides of the present invention each include a nucleic acid with a sequence selected from SEQ ID NOS: 2-4, 6, 8-10, 12, and 14-34, a substantially identical variant thereof in which the variant has at least, e.g., 80%, 90%, or 95% sequence identity to one of SEQ ID NOS: 2-4, 6, 8-10, 12, and 14-34, or a complement of SEQ ID NOS: 2-4, 6, 8-10, 12, and 14-34 and the variant.

TABLE I

| | Up Primers |
|---|---|
| SEQ ID NO | SEQUENCE |
| 2 | 5'-ACACCAATGAACCCTACGACC-3' |
| 8 | 5'-GATAAGCTTATTGAACAAGGACATCAA-3' |
| 12 | 5'-AAGATAAGCTTATTGAACAAGGACATC-3' |
| 14 | 5'-AGGCGTACATGGATATATCGGTAA-3' |
| 15 | 5'-GCTTATTGAACAAGGACATCAA-3' |
| 16 | 5'-GATAAGCTTATTGAACAAGGACATC-3' |
| 17 | 5'-ACACCAATGAACCCTACGAC-3' |
| 18 | 5'-ACACCAATGAACCCTACGA-3' |
| 19 | 5'-ACCAATGAACCCTACGACC-3' |
| 20 | 5'-ATACACAAACACCAATGAACCCTAC-3' |

TABLE II

| | Dn Primers |
|---|---|
| SEQ ID NO | SEQUENCE |
| 3 | 5'-TAATTGATCAATAAATGCTGTCAGA-3' |
| 6 | 5'-GATCAATAAATGCTGTCAGATGTTTAA-3' |
| 9 | 5'-CTTGAGGTGAATTGTTGTGAACC-3' |
| 21 | 5'-TGCTTGAGGTGAATTGTTGTGAA-3' |
| 22 | 5'-AGATAGCCTTGCTTGAGGTGAA-3' |
| 23 | 5'-CTTGAGGTGAATTGTTGTGAA-3' |

TABLE II-continued

Dn Primers

| SEQ ID NO | SEQUENCE |
|---|---|
| 24 | 5'-TGAGGTGAATTGTTGTGAACC-3' |
| 25 | 5'-CAATAAATGCTGTCAGATGTTTAA-3' |
| 26 | 5'-TAATTGATCAATAAATGCTGTCA-3' |

TABLE III

Probes

| SEQ ID NO | SEQUENCE |
|---|---|
| 4 | 5'-TTGCCCAGGAAATTTCCAACGGTT-3' |
| 10 | 5'-TTAGGAATCAATTATGGAAGTCGACCTCGT-3' |
| 27 | 5'-TGGTGCACATTGCCCAGGAAATTT-3' |
| 28 | 5'-CATTGCCCAGGAAATTTCCAACGGTT-3' |
| 29 | 5'-CCCAGGAAATTTCCAACGGTT-3' |
| 30 | 5'-CGAGGTCGACTTCCATAATTGATTCCT-3' |
| 31 | 5'-ACGAGGTCGACTTCCATAATTGATTCCTAA-3' |
| 32 | 5'-AAATTTCCTGGGCAATGTGCACCA-3' |
| 33 | 5'-AACCGTTGGAAATTTCCTGGGCAATG-3' |
| 34 | 5'-AACCGTTGGAAATTTCCTGGGCAA-3' |

TABLE IV

AMPLICONS

| SEQ ID NO | SEQUENCE |
|---|---|
| 5 | 5'-ACACCAATGA ACCCTACGAC CAACTATGGT ATTTCCAAAA AGTTCGCTGA ACAAGCATTA CAAGAATTGA TTAGTGATTC GTTTAAAGTA GCAATTGTGA GACCACCAAT GATTTATGGT GCACATTGCC CAGGAAATTT CCAACGGTTA ATGCAATTGT CAAAGCGATT GCCAATCATT CCCAATATTA ACAATCAGCG CAGTGCATTA TATATTAAAC ATCTGACAGC ATTTATTGAT CAATTA-3' |
| 7 | 5'-ACACCAATGA ACCCTACGAC CAACTATGGT ATTTCCAAAA AGTTCGCTGA ACAAGCATTA CAAGAATTGA TTAGTGATTC GTTTAAAGTA GCAATTGTGA GACCACCAAT GATTTATGGT GCACATTGCC CAGGAAATTT CCAACGGTTA ATGCAATTGT CAAAGCGATT GCCAATCATT CCCAATATTA ACAATCAGCG CAGTGCATTA TATATTAAAC ATCTGACAGC ATTTATTGAT C-3' |
| 11 | 5'-GATAAGCTTA TTGAACAAGG ACATCAAGTA GATCAAATTA ATGTTAGGAA TCAATTATGG AAGTCGACCT CGTTCAAAGA TTATGATGTT TTAATTCATA CAGCAGCTTT GGTTCACAAC AATTCACCTC AAG-3' |
| 13 | 5'-AAGATAAGCT TATTGAACAA GGACATCAAG TAGATCAAAT TAATGTTAGG AATCAATTAT GGAAGTCGAC CTCGTTCAAA GATTATGATG TTTTAATTCA TACAGCAGCT TTGGTTCACA ACAATTCACC TCAAG-3' |

In one embodiment of the invention, a particular set of CPE primers and probe is used in order to provide for detection of SA in a biological sample suspected of containing SA. The set of primers and probe may comprise at least one primer and probe specific for CPE comprising or consisting of a nucleic acid sequence selected from the group consisting of SEQ ID NOs: 2-4, 6, 8-10, 12, and 14-34, in another embodiment of the invention, the primer and for CPE comprises or consists of a functionally active variant of any of the primers of SEQ ID NOs: 2-4, 6, 8-10, 12, and 14-34.

A functionally active variant of any of the primers and/or probes of SEQ ID NOs: 2-4, 6, 8-10, 12, and 14-34 may be identified by using the primers and/or probes in the method of the invention. A functionally active variant of a primer and/or probe of any of the SEQ ID NOs: 2-4, 6, 8-10, 12, and 14-34 pertains to a primer which provides a similar or higher specificity and sensitivity in the method or kit of the invention as compared to the respective sequence of SEQ ID NOs: 2-4, 6, 8-10, 12, and 14-34.

The variant may, e.g., vary from the sequence of SEQ ID NOs: 2-4, 6, 8-10, 12, and 14-34 by one or more nucleotide additions, deletions or substitutions such as one or more nucleotide additions, deletions or substitutions at the 5' end and/or the 3' end of the respective sequence of SEQ ID NOs: 2-4, 6, 8-10, 12, and 14-34. As detailed above, a primer (and/or probe) may be chemically modified, i.e., a primer and/or probe may comprise as modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify as nucleic acid molecule encoding SA, e.g., nucleic acids encoding alternative portions of CPE, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g. 8, 10, 12, 14, 16, 18, 20, 22, 24, 26, 28, 30, 32, 34, 36, 38, 40, 42, 44, 46, 48, or 50 nucleotides in length).

In addition to a set of primers, the methods of the invention may use one or more probes in order to detect the presence or absence of SA. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a SA CPE (target) nucleic acid. A "probe" can be referred to as a "detection probe" meaning that it detects the target nucleic acid.

According to the invention, the CPE probe can be labeled with at least one fluorescent label. In one embodiment, the CPE probe can be labeled with a donor fluorescent moiety, e.g., a fluorescent dye, and a corresponding acceptor fluorescent moiety, e.g., a quencher.

In one embodiment of the present invention, at least one probe comprises or consists of a fluorescent moiety and a nucleic acid sequences selected from the group consisting of SEQ ID NOs: 4, 10, and 27-34 (shown without the label).

Designing oligonucleotides to be used as hybridization probes can be performed in a manner similar to the design of primers. Embodiments of the present invention may use a single probe or a pair of probes for detection of he amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g. 16, 18, 20, 21, 22, 23, 24, or 25) nucleotides in length.

Constructs of the present invention include vectors containing a SA CPE nucleic acid molecule (e.g., SEQ ID NOs: 2-4, 6, 8-10, 12, and 14-34). Constructs of the invention can be used, for example, as control template nucleic acid molecules. Vectors suitable for use in the present invention are commercially available and/or produced by recombinant nucleic acid technology methods routine in the art. SA CPE nucleic acid molecules can be obtained, for example, by chemical synthesis, direct cloning from SA, or by PCR amplification.

Constructs suitable for use in the methods of the invention typically include, in addition to SA CPE nucleic add molecules (e.g., a nucleic acid molecule that contains one or more sequences of SEQ ID NOs: 2-4, 6, 8-10, 12, and 14-34), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing CPE nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic add template (e.g., DNA or RNA). Primers useful in the present invention include oligonucleotides capable of acting as a point of initiation of nucleic acid synthesis within SA CPE nucleic acid sequences (e.g., SEQ ID NOs: 2, 3, 6, 8, 9, 12, and 14-27). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the CPE nucleic acid. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ SA nucleic acid such as RNA or DNA (cDNA). The template nucleic acid need not be purified; it may be a minor fraction of a complex mixture, such as SA nucleic acid contained in human cells. SA nucleic acids may be extracted from a biological sample by routine techniques such a those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources, including bacteria, yeast, viruses, organelles, or higher organisms such as plants or animals.

The oligonucleotide primers (e.g., SEQ ID NOs: 2, 3, 6, 8, 9, 12, and 14-27) are combined with PCR reagents under reaction conditions that induce primer extension. For example, chain extension reactions generally include 50 mM, KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target CPE nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with as different wavelength.

In one example, a oligonucleotide probe can contain a donor fluorescent moiety and a corresponding quencher, which dissipates the transferred energy in a form other than light. When the probe is intact, energy transfer typically occurs between the two fluorescent moieties such that fluorescent emission from the donor fluorescent moiety is quenched. During an extension step of a polymerase chain reaction, a probe bound to an amplification product is cleaved by the 5' to 3' exonuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quencher™ (BHQ), (Biosearch Technologies, Inc., Novato, Calif.), Ion Black™, (Integrated DNA Tech, Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the CPE target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer.

Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used include LC Red 640, LC Red 705, Cy5, Cy5.5, Lissamine rhodamine B sulfonyl chloride, tetramethyl rhodamine isothiocyanate, rhodaminexisothiocyanate, erythrosine isothiocyanate, fluorescein, diethylenetriamine pentaacetate, or other chelates of Lanthanide ions (e.g. Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of as linker arm for the purpose of the present invention is the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC Red 640-NHS-ester can be combined with C6-Phosphoramidites (available from ABI (Foster City, Calif.) or Glen Research (Sterling, Va.)) to produce, for example, LC Red 640-Phosphoramidite. Frequently used linkers to couple a donor fluorescent moiety such a fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPGs that require coupling of a fluorescein-NHS-ester after oligonucleotide synthesis.

Detection of *Staphylococcus aureus*

The present invention provides methods for detecting the presence or absence of SA in a biological or non-biological sample. Methods provided by the invention avoid problems of sample contamination, false negatives, and false positives. The methods include performing at least one cycling step that includes amplifying a portion of a SA CPE nucleic acid molecule from a sample using a pair of CPE primers, and a FRET detecting step. Multiple cycling steps are performed, preferably in a thermocycler. Methods of the invention can be performed using the CPE primers and probes to detect the presence of CPR, and the detection of CPE indicates the presence of a SA in the sample.

As described herein, amplification products can be detected using labeled hybridization probes that take advantage of FRET technology. One FRET format utilizes TaqMan® technology to detect the presence or absence of an amplification product, and hence, the presence or absence of SA. TaqMan® technology utilizes one single-stranded hybridization probe labeled with two fluorescent moieties. When as first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TaqMan® technology, and is suitable for performing the methods described herein for detecting the presence or absence of SA in the sample.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of SA genomes). If amplification of CPE nucleic acid occurs and an amplification product is produced, the step of hybridizing results in a detectable signal based upon FRET between the members of the pair of probes.

Generally, the presence of FRET indicates the presence of SA in the sample, and the absence of FRET indicates the absence of SA in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of a SA infection.

Representative biological samples that can be used in practicing the methods of the invention include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release SA nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the CPE probes from the CPE amplification product can confirm the presence or absence of SA in the sample.

Within each thermocycler run, control samples are cycled as well. Positive control samples can amplify SA nucleic, acid control template (other than CPE) using, for example, control primers and control probes. Positive control samples can also amplify, for example, a plasmid construct containing SA CPE nucleic acid molecules. Such a plasmid control can be an internally (e.g., within the sample) or in a separate sample run side-by-side with the patients samples. Each thermocycler run can also include a negative control that, for example, lacks SA template DNA. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,681,896 and 5,945,313 to reduce or eliminate contamination between one there run and the next.

Conventional PCR methods in conjunction with FRET technology can be used to practice the methods of the invention. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as nucleic acid intercalating the also elm be used. When double-stranded DNA binding dyes are used, a melting curve analysis is usually performed for confirmation of the presence of the amplification product.

It is understood that the present invention is not limited by the configuration of one or more commercially available instruments.

Articles of Manufacture/Kits

The present invention further provides for articles of manufacture or kits to detect SA. An article of manufacture according to the present invention can include primers and probes used to detect SA, together with suitable packaging materials. Representative primers and probes for detection of SA are capable of hybridizing to SA CPE nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to SA CPE nucleic acid molecules are provided.

Articles of manufacture of the invention can also include one or more fluorescent moieties for labeling the probes or alternatively, the probes supplied with the kit can be labeled. For example, an article of manufacture may include a donor fluorescent moiety for labeling one of the CPE probes and an acceptor fluorescent moiety for labeling the other CPE probe, respectively. Examples of suitable FRET donor fluorescent moieties and corresponding acceptor fluorescent moieties are provided above.

Articles of manufacture of the invention can also contain a package insert or package label having instructions thereon for using the CPE primers and probes to detect SA in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

The following examples and figures are provide to aid the understanding of the present invention, the true scope of which is set forth in the appended claims. It is understood that modifications can be made in the procedures set forth without departing from the spirit of the invention.

Example 1

Selection of the Capsular Polysaccharide Enzyme Gene Target

The CPE gene targeted was determined to be specific to *S. aureus* and not present in other *Staphylococcal* species by BLAST sequence analysis using whole genomes publicly available for *S. aureus* and several other *Staphylococcus* species.

Primer sites were chosen within the CPE gene that would yield amplicons less than 250 bp in length, and have either double dA or double dC nucleotides on the 3' end (if possible). Primers were also selected to have Tm's greater than 64° C., and made with a 3' t-butylbenzyl modifier to reduce primer dimer and increase specificity during PCR. After initial primer sites were chosen, they were BLAST searched to check for specificity to *S. aureus*, and evaluated using Oligo 6 Primer Analysis Software to check for the probability of primer dimer formation and false priming sites elsewhere in the CPE gene.

Homology of the CPE gene within *S. aureus* was verified by sequencing the CPE gene from 20 unique *S. aureus* isolates, as well as by BLAST searching public sequence databases. Exclusivity of each primer set was verified by amplification with other *Staphylococcal* species (*S. captis, S. hominis, S. haemolyticus, S. ludgunensis, S. carnosus, S. saprophyticus*, and *S. scirui*).

The CPE gene cap5N within *S. aureus* is about 880 base pairs long, and due to its unique presence and high homology in *S. aureus*, it is an ideal target for specificity and exclusivity to this organism. Several potential PCR amplicons were designed and tested for optimal performance within this gene, and the following four oligo set options yielded the most products (observed by gel electrophoresis), as well is the highest fluorescence and earliest elbow values observed by TaqMan® analysis.

CPE Oligo Set #1

```
                                                          (SEQ ID NO: 2)
Up Primer: ACACCAATGAACCCTACGACJ  (J = butylbenzyl dC)

(SEQ ID NO: 3)
Dn Primer: TAATTGATCAATAAATGCTGTCAGJ  (J = t-butylbenzyl dA)

(SEQ ID NO: 4)
Probe: ETTGCCCQAGGAAATTTCCAACGGTTP  (E = thFAM, Q = BHQ2, P = 3' phosphate)
```

Amplicon Generated from Oligo Set #1:

```
                                                          (SEQ IQ NO: 5)
ACACCAATGAACCCTACGACCAACTATGGTATTTCCAAAAAGTTCGCTGAACAAGCA

TTACAAGAATTGATTAGTGATTCGTTTAAAGTAGCAATTGTGAGACCACCAATGATT

TATGGTGCACATTGCCCAGGAAATTTCCAACGGTTAATGCAATTGTCAAAGCGATTG

CCAATCATTCCCAATATTAACAATCAGCGCAGTGCATTATATATTAAACATCTGACA

GCATTTATTGATCAATTA
```

CPE Oligo Set #2

```
                                                          (SEQ ID NO: 2)
Up Primer: ACACCAATGAACCCTACGACJ  (J = t-butylbenzyl dC)

(SEQ ID NO: 6)
Dn Primer: GATCAATAAATGCTGTCAGATGTTTAJ  (J = t-butylbenzyl dA)

(SEQ ID NO: 4)
Probe: ETTGCCCQAGGAAATTTCCAACGGTTP  (E = thFAM, Q = BHQ2, P = 3' phosphate)
```

Amplicon Generated from Oligo Set #2:

```
                                                          (SEQ ID NO: 7)
ACACCAATGAACCCTACGACCAACTATGGTATTTCCAAAAAGTTCGCTGAACAAGCA

TTACAAGAATTGATTAGTGATTCGTTTAAAGTAGCAATTGTGAGACCACCAATGATT

TATGGTGCACATTGCCCAGGAAATTTCCAACGGTTAATGCAATTGTCAAAGCGATTG

CCAATCATTCCCAATATTAACAATCAGCGCAGTGCATTATATATTAAACATCTGACA

GCATTTATTGATC
```

CPE Oligo Set #3

```
                                                          (SEQ ID NO: 8)
Up Primer: GATAAGCTTATTGAACAAGGACATCAJ  (J = t-butylbenzyl dA)

(SEQ ID NO: 9)
Dn Primer: CTTGAGGTGAATTGTTGTGAACJ  (J = t-butylbenzyl dC)

(SEQ ID NO: 10)
Probe: ETTAGGAQATCAATTATGGAAGTCGACCTCGTP  (E = thFAM, Q = BHQ2, P = 3' phosphate)
```

Amplicon Generated from Oligo Set #3:

(SEQ ID NO: 11)
GATAAGCTTATTGAACAAGGACATCAAGTAGATCAAATTAATGTTAGGAATCAATTA

TGGAAGTCGACCTCGTTCAAAGATTATGATGTTTTAATTCATACAGCAAGCTTTGGTT

CACAACAATTCACCTCAAG

CPE Oligo Set #4

Up Primer: AAGATAAGCTTATTGAACAAGGACATJ (J = t-butylbenzyl dC)  (SEQ ID NO: 12)

Dn Primer: CTTGAGGTGAATTGTTGTGAACJ (J = t-butylbenzyl dC)  (SEQ ID NO: 9)

Probe: ETTAGGAQATCAATTATGGAAGTCGACCTCGTP (E = thFAM, Q = BHQ2, P = 3' phosphate)  (SEQ ID NO: 10)

Amplicon Generated from Oligo Set #4:

(SEQ ID NO: 13)
AAGATAAGCTTATTGAACAAGGACATCAAGTAGATCAAATTAATGTTAGGAATCAAT

TATGGAAGTGGACCTCGTTCAAAGATTATGATGTTTTAATTCATACAGCAGCTTTGG

TTCACAACAATTCACCTCAAG

PCR Conditions:

25 µL of *S. aureus* genomic DNA diluted in 30 mM Tris, pH 8.5, plus 18 µL of master mix (154 mM Tricine, 110 mM Potassium Hydroxide, 190 mM Potassium Acetate, 19% Glycerol (v/v), 2.3% DMSO, 1.16 mM dATP, 1.16 mM dCTP, 1.16 mM dGTP, 1.16 mM dUTP, 1.0 µM upstream assay primer, 1.0 µM downstream assay primer, 0.185 µM probe, 3.08 U/mL ZO5 DNA polymerase, 150 U/mL UNG, 0.09% Sodium Azide (w/v), pH 8.50, plus 7 µL of activation mix (50 mM Magnesium chloride).

PCR Instrument:

LightCycler® 480 with Cobas® z480 filter configuration

Example 2

CPE Oligos Performance Evaluation Method

Figure 3B:
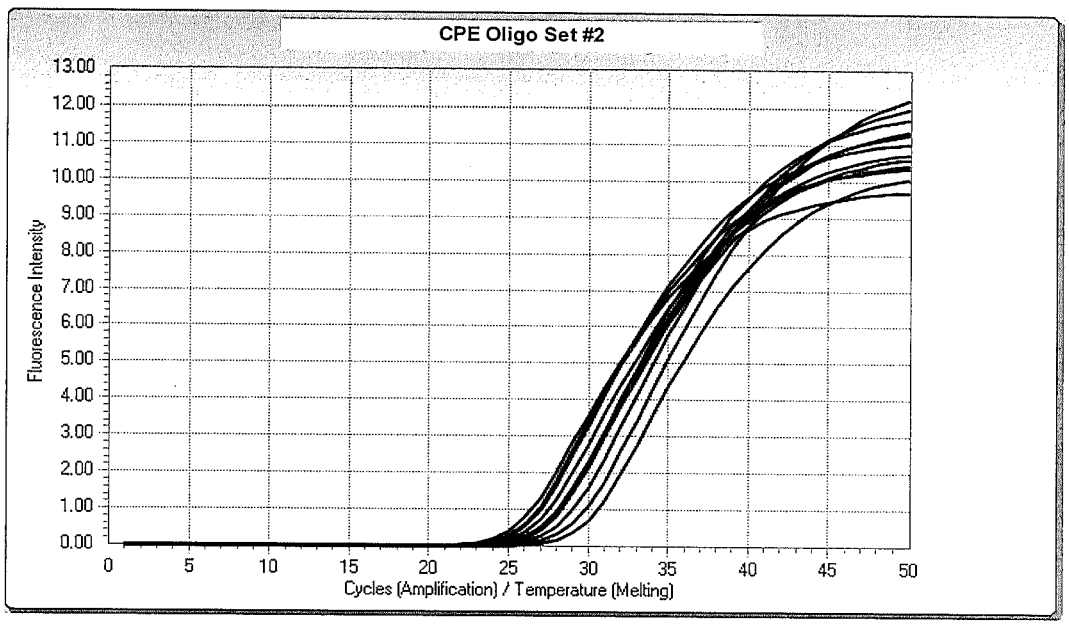
Figure 3C:
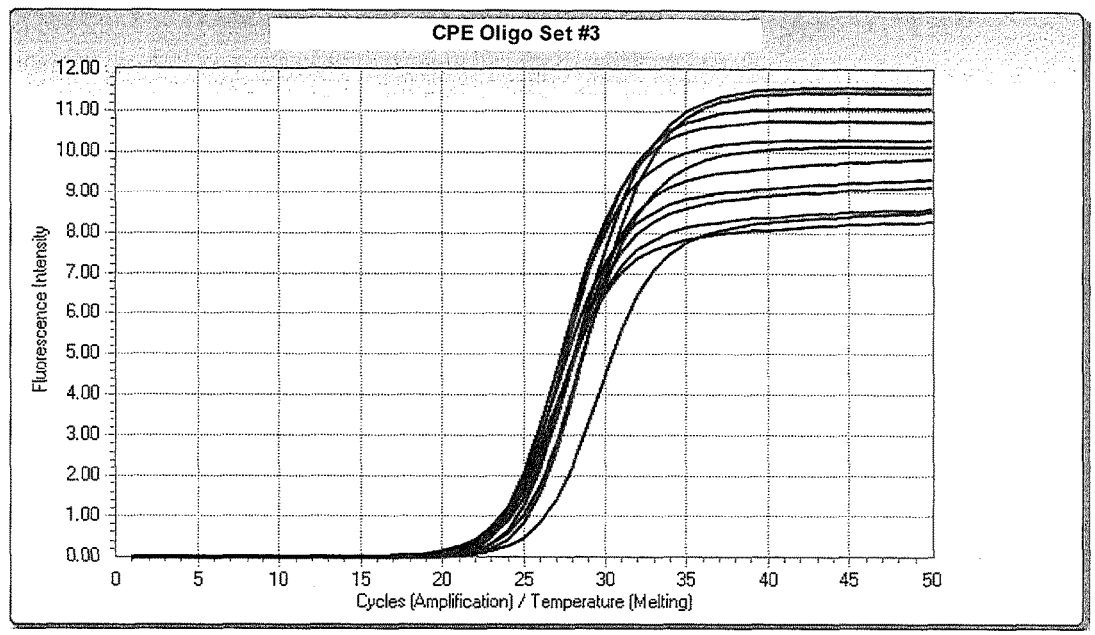
Figure 3D:
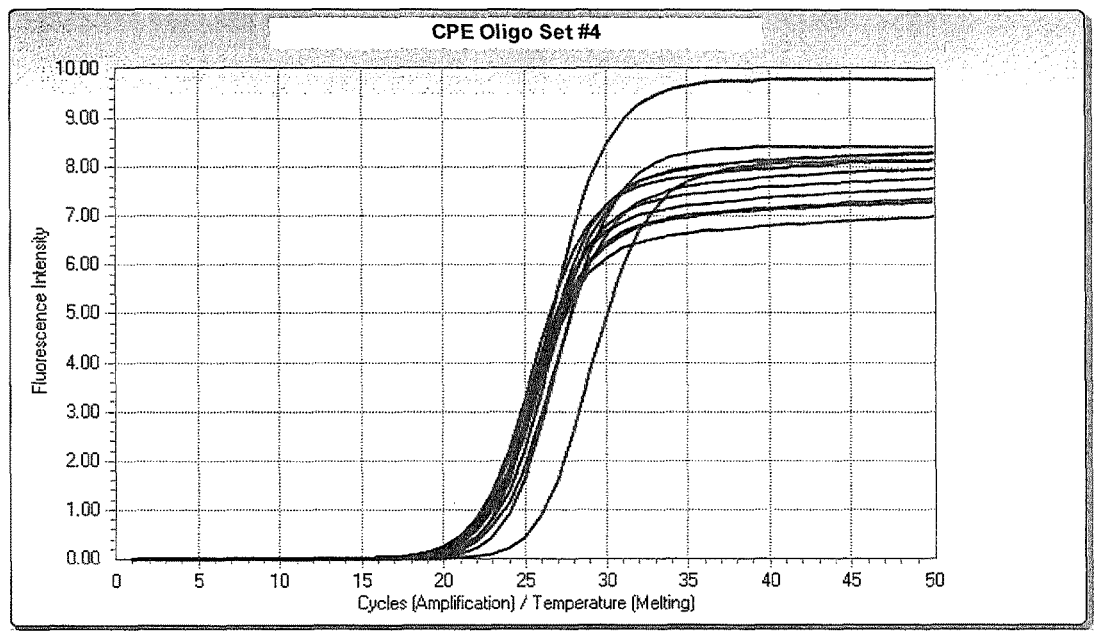

Referring to FIGS. 3A-3D, evaluation of the CPE oligo sets #1-4 occurred by evaluating genomic DNA from 12 unique, cultured *S. aureus* organisms. Genomic DNA from each *S. aureus* organism was diluted to ~105 c/PCR in 30 mM Tris, pH 8.5, and 25 µL of genomic DNA was added to 18 µL of pre-formulated master mix plus 7 µL of activation reagent. Pre-formulated master mix contained the following component concentrations: 154 mM Tricine, 110 mM Potassium Hydroxide, 190 mM Potassium Acetate, 19% Glycerol (v/v), 2.3% DMSO, 1.16 mM dATP, 1.16 mM dCTP, 1.16 mM dGTP, 1.16 mM dUTP, 1.0 µM upstream assay primer, 1.0 µM downstream assay primer, 0.185 µM probe, 308 U/mL ZO5 DNA polymerase, 150 U/mL UNG, 0.09% Sodium Azide (w/v), pH 8.50. Activation reagent contained 50 mM Magnesium chloride.

Example 3

Exclusivity Evaluation Method

Evaluation of the exclusivity of CPE oligo set #4 occurred by combining 1 µL of *Staph* sp. genomic DNA diluted to ~$10^6$ c/µL, in 30 mM Tris, pH 8.5, plus 50 µL of reconstituted master mix. Reconstituted master mix consisted of genomic DNA in 25 µL of 30 mM Tris, pH 8.5 plus 18 µL of pre-formulated master mix plus 7 µL of activation reagent (50 µL total volume). Pre-formulated master mix contained the following component concentrations: 154 mM Tricine, 110 mM Potassium Hydroxide, 190 mM Potassium Acetate, 19% Glycerol (v/v), 2.3% DMSO, 1.16 mM dATP, 1.16 mM dCTP, 1.16 mM dGTP, 1.16 mM dUTP, 1.0 µM upstream CPE primer, 1.0 µM downstream CPE primer, 5.0 uM other assay primers (not CPE targets), 0.185 µM CPE target probe, 1.0 uM other assay probes (not CPE targets), 308 U/mL ZO5 DNA polymerase, 150 U/mL UNG, 0.09% Sodium Azide (w/v), pH 8.50. Activation reagent contained 50 mM Magnesium chloride.

| CPE Oligo Set #4 | | |
|---|---|---|
| Organism | ID | Ct's |
| *S. capitis* | 1194 | −1 |
| *S. capitis* | 3104 | −1 |
| *S. capitis* | 5662 | −1 |
| *S. capitis* | 10728 | −1 |
| *S. capitis* | 10729 | −1 |
| *S. capitis* | 10730 | −1 |

CPE Oligo Set #4

| Organism | ID | Ct's |
|---|---|---|
| S. capitis | 10731 | −1 |
| S. capitis | 10732 | −1 |
| S. capitis | 10733 | −1 |
| S. saprophyticus | 10738 | −1 |
| S. saprophyticus | 10740 | −1 |
| S. sciuri | 323 | −1 |
| S. sciuri | 10741 | −1 |
| S. aureus (ctrl) | 10710 | 29.42 |
| S. aureus (ctrl) | 10714 | 28.54 |
| S. haemolyticus | 6760 | −1 |
| S. haemolyticus | 6762 | −1 |
| S. haemolyticus | 10734 | −1 |
| S. haemolyticus | 10735 | −1 |
| S. haemolyticus | 10736 | −1 |
| S. haemolyticus | 10737 | −1 |
| S. haemolyticus | 1207 | −1 |
| S. judgunensis | 5743 | −1 |
| S. judgunensis | 7039 | −1 |
| S. judgunensis | 10739 | −1 |
| S. hominis | 3106 | −1 |
| S. hominis | 5651 | −1 |

CPE Oligo Set #4

| Organism | ID | Ct's |
|---|---|---|
| S. hominis | 10742 | −1 |
| S. hominis | 10743 | −1 |
| S. hominis | 10744 | −1 |
| S. hominis | 10745 | −1 |
| S. epidermidis | 5657 | −1 |

While the foregoing invention has been described in some detail for purposes of clarity and understanding, it will be clear to one skilled in the art from a reading of this disclosure that various changes in form and detail can be in without deputing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

---

What is claimed:

1. A method of detecting *Staphylococcus aureus* (SA) in a sample, the method comprising:

performing an amplifying step comprising contacting the sample with a set of SA primers to produce an amplification product of the Capsular Polysaccharide Enzyme (CPE) gene if SA is present in the sample whether or not SA is methicillin resistant;

performing a hybridizing step comprising contacting the amplification product of the CPE gene with one or more detectable SA probes; and detecting the presence or absence of the amplified product of the CPE gene, wherein the presence of the amplified product of the CPE gene is indicative of the presence of SA in the sample whether or not SA is methicillin resistant, and wherein the absence of the amplified product of the CPE gene is indicative of the absence of SA in the sample whether or not SA is methicillin resistant;

wherein the set of SA primers comprise a first primer consisting of the sequence of SEQ ID NO: 2, or the complete complement thereof, and a second primer consisting of the sequence of SEQ ID NO: 3, or the complete complement thereof;

wherein the amplification product of the CPE gene produced by the set of SA primers consists of the sequence of SEQ ID NO: 5; and wherein the one or more detectable SA probes comprise at least one detectable SA probe consisting of the sequence of SEQ ID NO: 4, or the complete complement thereof.

2. The method of claim 1, wherein:

the hybridizing step comprises contacting the amplification product of the CPE gene with the detectable SA probe that is labeled with a donor fluorescent moiety and a corresponding acceptor fluorescent moiety; and the detecting step comprises detecting the presence or absence of fluorescence resonance energy transfer (FRET) between the donor fluorescent moiety and the acceptor fluorescent moiety of the probe, wherein the presence or absence of fluorescence is indicative of the presence or absence of SA in the sample.

3. The method of claim 2, wherein said amplification employs a polymerase enzyme having 5' to 3' exonuclease activity.

4. The method of claim 3, wherein said donor fluorescent moiety and said acceptor fluorescent moiety are within no more than 5 nucleotides of each other on said probe.

5. The method of claim 4, wherein said acceptor fluorescent moiety is a quencher.

* * * * *

SEQUENCE LISTING

<160> NUMBER OF SEQ ID NOS: 34

<210> SEQ ID NO 1
<211> LENGTH: 888
<212> TYPE: DNA
<213> ORGANISM: Staphylococcus aureus

<400> SEQUENCE: 1

```
atgagaaaaa atattttaat tacaggcgta catggatata tcggtaatgc tttaaaagat      60
aagcttattg aacaaggaca tcaagtagat caaattaatg ttaggaatca attatggaag     120
tcgacctcgt tcaaagatta tgatgtttta attcatacag cagctttggt tcacaacaat     180
tcacctcaag caaggctatc tgattatatg caagtgaata tgttgctgac gaaacaattg     240
gcacaaaagg ctaaagctga agacgttaaa caatttattt ttatgagtac tatggcagtt     300
tatggaaaag aaggtcatgt tggtaaatca gatcaagttg atacacaaac accaatgaac     360
cctacgacca actatggtat ttccaaaaag ttcgctgaac aagcattaca agaattgatt     420
agtgattcgt ttaaagtagc aattgtgaga ccaccaatga tttatggtgc acattgccca     480
ggaaatttcc aacggttaat gcaattgtca aagcgattgc caatcattcc caatattaac     540
aatcagcgca gtgcattata tattaaacat ctgacagcat ttattgatca attaatatca     600
ttagaagtga caggtgtgta ccatcctcaa gatagttttt actttgatac atcgtcagta     660
atgtatgaaa tacgtcgcca atcacatcgt aaaacggtat tgatcaacat gccttcaatg     720
ctaaataagt attttaataa gttgtcggtc tttagaaaat tattcggcaa tttaatatac     780
agcaatacgt tatatgaaaa taataatgca cttgaaatta ttcctggaaa aatgtcactt     840
gttattgcgg acatcatgga tgaaacgaca accaaagata aggcataa                   888
```

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2

```
acaccaatga accctacgac c                                              21

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide

<400> SEQUENCE: 3
taattgatca ataaatgctg tcaga                                          25

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide

<400> SEQUENCE: 4
ttgcccagga aatttccaac ggtt                                           24

<210> SEQ ID NO 5
<211> LENGTH: 246
<212> TYPE: DNA
<213> ORGANISM: Artificial Sequence
<220> FEATURE:
<223> OTHER INFORMATION: Oligonucleotide

<400> SEQUENCE: 5
acaccaatga accctacgac caactatggt atttccaaaa agttcgctga acaagcatta    60
caagaattga ttagtgattc gtttaaagta gcaattgtga gaccaccaat gatttatggt   120
gcacattgcc caggaaattt ccaacggtta atgcaattgt caaagcgatt gccaatcatt   180
cccaatatta caatcagcg cagtgcatta tatattaaac atctgacagc atttattgat    240
caatta                                                             246

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide

<400> SEQUENCE: 6
gatcaataaa tgctgtcaga tgtttaa                                        27

<210> SEQ ID NO 7
<211> LENGTH: 241
<212> TYPE: DNA
<213> ORGANISM: Artificial Sequence
<220> FEATURE:
<223> OTHER INFORMATION: Oligonucleotide

<400> SEQUENCE: 7
acaccaatga accctacgac caactatggt atttccaaaa agttcgctga acaagcatta    60
caagaattga ttagtgattc gtttaaagta gcaattgtga gaccaccaat gatttatggt   120
gcacattgcc caggaaattt ccaacggtta atgcaattgt caaagcgatt gccaatcatt   180
cccaatatta caatcagcg cagtgcatta tatattaaac atctgacagc atttattgat    240
c                                                                  241
```

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide

<400> SEQUENCE: 8
gataagctta ttgaacaagg acatcaa                                         27

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide

<400> SEQUENCE: 9
cttgaggtga attgttgtga acc                                             23

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide

<400> SEQUENCE: 10
ttaggaatca attatggaag tcgacctcgt                                      30

<210> SEQ ID NO 11
<211> LENGTH: 133
<212> TYPE: DNA
<213> ORGANISM: Artificial Sequence
<220> FEATURE:
<223> OTHER INFORMATION: Oligonucleotide

<400> SEQUENCE: 11
gataagctta ttgaacaagg acatcaagta gatcaaatta atgttaggaa tcaattatgg     60
aagtcgacct cgttcaaaga ttatgatgtt ttaattcata cagcagcttt ggttcacaac    120
aattcacctc aag                                                       133

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide

<400> SEQUENCE: 12
aagataagct tattgaacaa ggacatc                                         27

<210> SEQ ID NO 13
<211> LENGTH: 135
<212> TYPE: DNA
<213> ORGANISM: Artificial Sequence
<220> FEATURE:
<223> OTHER INFORMATION: Oligonucleotide

<400> SEQUENCE: 13
aagataagct tattgaacaa ggacatcaag tagatcaaat taatgttagg aatcaattat     60
ggaagtcgac ctcgttcaaa gattatgatg ttttaattca tacagcagct ttggttcaca    120
acaattcacc tcaag                                                      135

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide

<400> SEQUENCE: 14
aggcgtacat ggatatatcg gtaa                                            24

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide

<400> SEQUENCE: 15
gcttattgaa caaggacatc aa                                              22

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide

<400> SEQUENCE: 16
gataagctta ttgaacaagg acatc                                           25

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
acaccaatga accctacgac                                                 20

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide

<400> SEQUENCE: 18
acaccaatga accctacga                                                  19

<210> SEQ ID NO 19
<211> LENGTH: 19
<212> TYPE: DNA
<213> ORGANISM: Artificial Sequence
<220> FEATURE:
<223> OTHER INFORMATION: Oligonucleotide

<400> SEQUENCE: 19
accaatgaac cctacgacc                                                  19

<210> SEQ ID NO 20
<211> LENGTH: 25
<212> TYPE: DNA
<213> ORGANISM: Artificial Sequence
<220> FEATURE:

<223> OTHER INFORMATION: Oligonucleotide

<400> SEQUENCE: 20
atacacaaac accaatgaac cctac                                    25

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide

<400> SEQUENCE: 21
tgcttgaggt gaattgttgt gaa                                      23

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide

<400> SEQUENCE: 22
agatagcctt gcttgaggtg aa                                       22

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide

<400> SEQUENCE: 23
cttgaggtga attgttgtga a                                        21

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide

<400> SEQUENCE: 24
tgaggtgaat tgttgtgaac c                                        21

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide

<400> SEQUENCE: 25
caataaatgc tgtcagatgt ttaa                                     24

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide

<400> SEQUENCE: 26
taattgatca ataaatgctg tca                                      23

```
<210> SEQ ID NO 27
<211> LENGTH: 24
<212> TYPE: DNA
<213> ORGANISM: Artificial Sequence
<220> FEATURE:
<223> OTHER INFORMATION: Oligonucleotide

<400> SEQUENCE: 27
tggtgcacat tgcccaggaa attt                                          24

<210> SEQ ID NO 28
<211> LENGTH: 26
<212> TYPE: DNA
<213> ORGANISM: Artificial Sequence
<220> FEATURE:
<223> OTHER INFORMATION: Oligonucleotide

<400> SEQUENCE: 28
cattgcccag gaaatttcca acggtt                                        26

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide

<400> SEQUENCE: 29
cccaggaaat tccaacggt t                                              21

<210> SEQ ID NO 30
<211> LENGTH: 27
<212> TYPE: DNA
<213> ORGANISM: Artificial Sequence
<220> FEATURE:
<223> OTHER INFORMATION: Oligonucleotide

<400> SEQUENCE: 30
cgaggtcgac ttccataatt gattcct                                       27

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide

<400> SEQUENCE: 31
acgaggtcga cttccataat tgattcctaa                                    30

<210> SEQ ID NO 32
<211> LENGTH: 24
<212> TYPE: DNA
<213> ORGANISM: Artificial Sequence
<220> FEATURE:
<223> OTHER INFORMATION: Oligonucleotide

<400> SEQUENCE: 32
aaatttcctg ggcaatgtgc acca                                          24

<210> SEQ ID NO 33
<211> LENGTH: 26
<212> TYPE: DNA
<213> ORGANISM: Artificial Sequence
<220> FEATURE:
<223> OTHER INFORMATION: Oligonucleotide
```

```
<400> SEQUENCE: 33
aaccgttgga aatttcctgg gcaatg                                        26

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide

<400> SEQUENCE: 34
aaccgttgga aatttcctgg gcaa                                          24
```